(12) United States Patent
Condemi

(10) Patent No.: US 11,426,424 B2
(45) Date of Patent: Aug. 30, 2022

(54) MOLECULAR OXYGEN AND HYALURONIC ACIDS FOR TOPICAL-VAGINAL USES

(71) Applicant: Tricomef S.r.l., Sala Bolognese (IT)

(72) Inventor: Leone Condemi, Sala Bolognese (IT)

(73) Assignee: CARESS FLOW S.r.l., Bologna (IT)

( * ) Notice: Subject to any disclaimer, the term of this patent is extended or adjusted under 35 U.S.C. 154(b) by 173 days.

(21) Appl. No.: 16/625,568

(22) PCT Filed: Jun. 20, 2018

(86) PCT No.: PCT/IB2018/054527
§ 371 (c)(1),
(2) Date: Dec. 20, 2019

(87) PCT Pub. No.: WO2019/003053
PCT Pub. Date: Jan. 3, 2019

(65) Prior Publication Data
US 2021/0353663 A1    Nov. 18, 2021

(30) Foreign Application Priority Data

Jun. 26, 2017   (IT) .................. 102017000070951

(51) Int. Cl.
*A61K 33/00* (2006.01)
*A61K 9/00* (2006.01)
*A61K 31/728* (2006.01)

(52) U.S. Cl.
CPC .......... *A61K 31/728* (2013.01); *A61K 9/0034* (2013.01); *A61K 33/00* (2013.01)

(58) Field of Classification Search
CPC ..... A61K 31/728; A61K 9/0034; A61K 33/00
USPC .......................................................... 514/54
See application file for complete search history.

(56) References Cited

PUBLICATIONS

Walker et al, Radiographics, 2011, 1-23.*
Chen et al, J Sex Med., 2013, 10, 1575-1584.*
Minnesota Pollution Control Agency, 2009, pp. 1-2.*
International Search Report and Written Opinion of the International Searching Authority, dated Oct. 9, 2018, in related International Application No. PCT/IB2018/054527, 11 pages.
Chen et al., "Evaluation of the Efficacy and Safety of Hyaluronic Acid Vaginal Gel to Ease Vaginal Dryness: A Multicenter, Randomized, Controlled, Open-Label, Parallel-Group, Clinical Trial", Journal of Sexual Medicine: International Society for Sexual Medicine, 2013, vol. 10, No. 6 (Apr. 9, 2013), 10 pages.
Asadamongkol et al., "The development of hyperbaric oxygen therapy for skin rejuvenation and treatment of photoaging", Medical Gas Research: BioMed Central Ltd., vol. 4, No. 1 (Apr. 1, 2014), 6 pages.

* cited by examiner

*Primary Examiner* — Ganapathy Krishnan
(74) *Attorney, Agent, or Firm* — MH2 Technology Law Group LLP

(57) ABSTRACT

A method for treatment of vaginal disorders may include: administering topically to a subject in need thereof a therapeutically effective amount of molecular oxygen and hyaluronic acid. The molecular oxygen may be in gaseous form. The vaginal disorders may be selected between vaginal dryness and vulvovaginal atrophy.

12 Claims, No Drawings

MOLECULAR OXYGEN AND HYALURONIC ACIDS FOR TOPICAL-VAGINAL USES

CROSS-REFERENCE TO RELATED APPLICATION(S)

This application is a national stage entry from International Application No. PCT/IB2018/054527, filed on Jun. 20, 2018, in the Receiving Office ("RO/IB") of the International Bureau of the World Intellectual Property Organization ("WIPO"), and published as International Publication No. WO 2019/003053 A1 on Jan. 3, 2019. International Application No. PCT/IB2018/054527 claims priority from Italian Patent Application No. 102017000070951, filed on Jun. 26, 2017, in the Italian Patent and Trademark Office ("IPTO"). The entire contents of all of these patent applications and publications are incorporated herein by reference.

FIELD OF THE INVENTION

The present patent application concerns a combination of active ingredients suitable for topical-vaginal administration and preferably used for the treatment of vaginal dryness and vulvovaginal atrophy.

PRIOR ART

Vaginal dryness is a disorder afflicting women of all ages, but which is especially common during and after menopause.

Besides causing itching, irritation of the mucous membranes, annoying secretions and bad odour, vaginal dryness is particularly felt by women at the time of penetration, during sexual intercourse, when it can cause pain and in some cases (microscopic, but very painful) abrasions on the vaginal mucosa.

The lesions can be complicated with annoying burning sensations, accompanied by bladder disorders and burning during urination, and even with a cystitis, which may appear 24-72 hours after intercourse.

Vaginal dryness mainly implies a lack of physiological local lubrication, whose causes are numerous and include, for example, advancing age, hormonal changes, menopause, breastfeeding, stress, conditions such as diabetes, irritable bowel syndrome, chronic heart failure and iatrogenic causes such as radiotherapy and chemotherapy or the use of antidepressants (D. Edwards and N. Panay. *Treating vulvovaginal atrophy/genitourinary syndrome of menopause: how important is vaginal lubricant and moisturizer composition?*. Taylor & Francis Climacteric.; 19(2): 151-161.)

During fertility, oestrogens plays a key role in keeping the vaginal environment functional.

The vaginal epithelium is a stratified squamous epithelium, which is lubricated, thick and rough, until menopause. At the menopause, with the decrease in oestrogen levels, vaginal epithelium becomes thinner. A reduction in epithelial cells leads to a reduction of cell exfoliation in the vagina, a process that normally has the function of releasing glycogen, which is hydrolysed into lactic acid by the action of lactobacilli, normally present in the vaginal flora.

Without the release of glycogen and without the production of lactic acid, the pH of the vagina increases, resulting in an alteration of the local flora and in a growth of harmful bacteria that can cause infections and inflammation.

Furthermore, the elasticity of the vaginal tissue is reduced, the connective tissue is increased and the vaginal blood flow decreases, with a consequent reduction of local lubrication (Maire B. Mac Bride, MBBCh, Deborah J. Rhodes, M D, and Lynne T. Shuster, M D *Vulvovaginal Atrophy* Mayo Clin Proc. 2010 January; 85(1): 87-94.).

The thinning and the inflammation of the vaginal and vulvar walls together contribute to reduce vaginal lubrication.

After three years since the last menstrual cycle, 47% of women suffer from vaginal dryness, a percentage that rises to almost all women 10 years after the beginning of menopause (Parish S et al. *"Impact of vulvovaginal health on postmenopausal women: a review of surveys on symptoms of vulvovaginal atrophy."* International Journal of Women's Health 2013; 5; 437-444), with the exception of the obese, whose adipose tissue produces oestrone, an oestrogen that attenuates dryness but which is dangerous as it increases the risk of breast and uterine tumours (endometrium), more common in overweight women.

All these problems lead women to avoid intimacy due to what in medical terms is called "vulvovaginal atrophy" (VVA).

Vaginal dryness is frequently reported as one of the symptoms associated with VVA, with a frequency of 15% of cases during pre-menopause and a frequency of 57% of cases after menopause.

VVA is registered under hypoestrogenic conditions. In the pre-menopausal state, estradiol levels fluctuate from 10 to 800 pg/mL, depending on when measured during the cycle. In the post-menopausal state, estradiol levels are typically below 30 pg/mL (Maire B. Mac Bride, MBBCh, Deborah J. Rhodes, M D, and Lynne T. Shuster, M D, *Vulvovaginal Atrophy*. Mayo Clin Proc. 2010 January; 85 (1): 87-94.).

VVA symptoms can be successfully treated by using over-the-counter medications, where the choice of therapy depends on the severity of the symptoms, the effectiveness of the therapy and the patient's preferences.

Lubricants can alleviate vaginal dryness during sexual intercourse, providing momentary relief from vaginal dryness and dyspareunia.

Unfortunately, the problem of vaginal dryness is little known, poorly diagnosed and poorly treated.

Women do not link symptoms to oestrogen deficiency. In fact, only 4% of women attribute vaginal dryness, pain during sexual intercourse and burning to vaginal atrophy; only 12% attribute them to hormonal changes and only 24% attribute them to menopause.

As many as 63% of women think that the disorders "will pass over time", without realizing that without oestrogen the accelerated aging of the tissues will continue. As a result, few women require a help from their doctor with a specific therapy.

Even doctors, however, have a strong responsibility in this "silent collusion". More than 50% of them do not even ask if the problem exists and, even if the woman talks about it, the therapeutic response is satisfactory only in 14% of cases.

The most effective treatments are hormonal ones, where the first choice of therapy is the administration of local oestrogens, including estriol, which is much lighter than estradiol and can be used for years, promestriene and conjugated oestrogens.

If there are also problems of dryness and a lower physical response of the external genitalia, a local testosterone ointment (galenic, by prescription) rekindles even more the physical response.

Local hormone therapy can solve the problems of dryness and genital atrophy in 85% of women after menopause. It is better if the treatment starts immediately after the disappearance of the menstrual cycle.

10-12% of women cannot use oestrogens, even local, because they have been operated for a breast cancer or an adenocarcinoma of the ovary or uterus. To reduce dryness and pain in these subjects it is possible to use vaginal hyaluronic acid, which has an excellent restorative and antioxidant action, vaginal laser, much more expensive, or different creams that do not have the therapeutic impact of hormones.

Hyaluronic acid has remarkable adhesive, moisturizing and reparative effects on vaginal mucosa. The use of hyaluronic acid in the treatment of vaginal dryness through the use of vaginal lavages or suppositories is known in the state of the art.

The use of vaginal lavages based on hyaluronic acid is considered a therapeutic alternative to treatments based on oestrogen for alleviating the problems associated with vaginal dryness. (Chen J et al. "Evaluation of the effectiveness and safety of hyaluronic acid vaginal gel to ease vaginal dryness: a multicentre, randomized, controlled, open-label, parallel-group, clinical trial." J Sex Med. 2013; 10; 1575-84

SUMMARY OF THE INVENTION

The Applicant has now found that an association comprising molecular oxygen and hyaluronic acid is particularly effective in the topical treatment of vaginal disorders. More preferably, the association object of the invention is used in the treatment of vaginal dryness and vulvovaginal atrophy.

DETAILED DESCRIPTION OF THE INVENTION

Vaginal disorders are typical intimate disorders of female genitalia, which occur at an early age, in adulthood or during maturity.

Vaginal disorders can be identified by a specific clinical picture (bacterial, viral, fungal infections; irritative, allergic or psychosomatic vaginitis) or may show up as one or more symptoms resulting from an imbalance of local and systemic homeostasis (dryness, burning, itching, leucorrhoea, redness, irritation and swelling). For the purposes of the present invention, vaginal disorders are preferably selected between vaginal dryness and vulvovaginal atrophy.

Oxygen has long been used for therapeutic purposes for the treatment of conditions such as decompression syndrome and carbon monoxide poisoning.

Recently, oxygen has started to be used in cosmetics for skin rejuvenation, for the treatment of photo-induced skin aging and for the improvement of skin complexion. Exposure to oxygen therapy of open wounds on pigskin showed an increase in the pO2 of the injured surface tissue. Repeated treatments accelerate the skin's healing, and wounds treated with oxygen show an increase in neoangiogenesis and tissue oxygenation. It is therefore believed that molecular oxygen reactivates microcirculation, thus activating red blood cells and favouring neoangiogenesis (Fries R B, Wallace W A, Roy S, Kuppusamy P, Bergdall V, Gordillo G M, Melvin W S, Sen C K (2005) Dermal excisional wound healing in pigs following treatment with topically pure oxygen, Mutat Res 579: 172-181).

Besides the reparative and regenerative effects (Roth V, Herron M S, et al., Stimulating angiogenesis by hyperbaric oxygen in an isolated tissue construct. Undersea Hyperb Med 2011, 38 (6): 509-514), molecular oxygen stimulates the epidermal turnover, thus improving hydration and tissue elasticity.

The oxygen present in the association object of the present invention advantageously works as a vehicle for hyaluronic acid and at the same time as an "enhancer" of the permeability of hyaluronic acid, thus stimulating local microcirculation as well as tissue regeneration and facilitating protein absorption through vaginal mucosa.

The oxygen contained in the combination of the present invention preferably has a purity comprised between 80% and 97% by volume (v/v).

The purified oxygen can be obtained by techniques known to those skilled in the art, such as by using a compressed air generator, which filters the outdoor air and purifies it from the components it contains in order to increase the oxygen volume percentage out of the total volume of air.

In the preferred embodiment, the purified oxygen is administered simultaneously with hyaluronic acid.

Preferably, sodium hyaluronate is administered together with said purified oxygen for a time ranging from 5 min to 15 min.

Preferably, oxygen is administered even before co-administration with hyaluronic acid, in order to condition the vaginal environment and improve local blood circulation.

Said prior conditioning has a duration preferably comprised between 3 min and 10 min.

Molecular oxygen is preferably administered at the topical-vaginal level at a flow rate ranging from 0.1 L/min to 5 L/min.

The hyaluronic acid contained in the combination preferably has a molecular weight ranging from 200 kDa to 2 MDa.

In the preferred embodiment, hyaluronic acid is in the form of a biologically acceptable alkaline metal salt, and even more preferably, in the form of sodium hyaluronate.

In order to convey hyaluronic acid by means of oxygen therapy (purified molecular oxygen), said hyaluronic acid is preferably dissolved in an aqueous solution, whose concentration is preferably between 0.05% and 0.3% (w/v) by weight if compared to the water volume.

In the preferred embodiment, sodium hyaluronate is administered at a dosage preferably comprised between 10 mg and 100 mg per unit of volume of purified oxygen, where the maximum volume of administered oxygen is preferably between 1.5 L and 75 L.

The association object of the present patent application can be administered continuously, according to the needs of the patient, and with dosing intervals preferably comprised between 20 and 30 days and even more preferably between 6 and 10 days.

An administration protocol for the association object of the present invention, together with the effectiveness data obtained from the same, is described for illustrative and non-limiting purposes.

Examples

Protocol

The protocol provides four administrations at intervals of 20 to 30 days, each lasting 15 minutes.

The treatment is carried out by using a device known under the trade name Exea X2, which transforms air into 95% pure oxygen.

The Exea X2 device consists of:

Compressor: a compressed air generator with the function of taking in air from the external environment, filtering and compressing it.

Machine body: equipped with zeolite molecular sieves. It exploits the principle of different absorption of gas molecules by different surfaces, allowing $O_2$ to pass through and retaining the other gases present in the air, such as nitrogen, argon, helium and hydrogen. The machine body transforms the outdoor air into 95% pure oxygen.

Dispenser: consisting of a vaginal cannula, connected to the machine body. The cannula is equipped with outlet holes for the delivery of oxygen and hyaluronic acid, which is inserted through a special injection valve, located in the upper part of the cannula.

The hyaluronic acid is previously dissolved in distilled water so as to form a 0.2% (w/v) solution.

The treatment begins with the introduction, for a period of 5 minutes, of purified oxygen, to condition the vaginal environment.

At the end of the 5 minutes of conditioning, the treatment involves the introduction of the hyaluronic acid solution by injecting it into the appropriate valve of the vaginal cannula, together with the oxygen supply, for a duration of 10 minutes.

Effectiveness Analysis

The aforementioned protocol has been tested on a sample of ten patients, aged between 42 and 60 years. Each of the patients subjected to the protocol has been affected by vaginal atrophy for more than a year and has had a PAP test in the last year.

The protocol provides a follow-up visit after 15 days and after 20 days from the treatment, when data on the effectiveness of the treatment are collected.

The effectiveness evaluation is performed by using a Visual Analogue Scale (VAS) with the following parameters:

Feeling of well-being—Parameter measured by means of a questionnaire to the patient, with an evaluation scale from 1 to 5, where 1 represents "no sensation of well-being" and 5 "maximum sensation of well-being".

Vaginal burning—Parameter measured by means of a questionnaire to the patient, with an evaluation scale from 1 to 5, where 1 represents "no improvement" and 5 "much improved".

Fluidity—Parameter measured by means of a questionnaire to the patient, with an evaluation scale from 1 to 5, where 1 represents "none" and 5 "normal".

pH—Evaluated in quintiles, with the following intervals:

| Vaginal pH goodness (physiological pH ~4.6) | | | | |
|---|---|---|---|---|
| No | Little | Average | Good | Excellent |
| pH >6 | 5-6 | 5 | 4.7-5 | >4.7 |

Vaginal epithelium—Evaluated as follows:

| Flushed - petechiae | Bleeding on contact | Bleeding on scraping | Not flushed | Normal |
|---|---|---|---|---|

Results

From the evaluation of effectiveness on ten patients undergoing treatment, the following emerged.

| | | | | | | |
|---|---|---|---|---|---|---|
| Feeling of well-being | Scoring scale | 1 | 2 | 3 | 4 | 5 |
| | Evaluation of patients | 0 | 0 | 0 | 1 | 9 |
| Vaginal burning | Scoring scale | 1 | 2 | 3 | 4 | 5 |
| | Evaluation of patients | 0 | 0 | 0 | 1 | 9 |
| Fluidity | Scoring scale | 1 | 2 | 3 | 4 | 5 |
| | Evaluation of patients | 0 | 0 | 0 | 1 | 9 |
| pH | Scoring scale | >6 | 5-6 | 5 | 4.7-5 | >4.7 |
| | Evaluation of patients | 0 | 0 | 0 | 0 | 10 |
| Vaginal epithelium | Scoring scale | Flushed - petechiae | Bleeding on contact | Bleeding on scraping | Not flushed | Normal |
| | Evaluation of patients | 0 | 0 | 0 | 0 | 10 |

CONCLUSIONS

The sensation described by the patients is one of immediate well-being.

At follow-up visits after 15 and 20 days, the lubrication effect persisted and all reported that during sexual intercourse they had no more of that pain that had previously prevented a normal couple life.

Only one patient reported a marked improvement, but still had a slight burning sensation. However, the patient wanted to complete the therapy, based on the results achieved up to that point.

The invention claimed is:

1. A method for treatment of vaginal disorders, the method comprising:
   administering topically to a subject in need thereof a therapeutically effective amount of molecular oxygen and hyaluronic acid;
   wherein the molecular oxygen is in gaseous form, and
   wherein the vaginal disorders are selected from the group consisting of vaginal dryness and vulvovaginal atrophy.

2. The method of claim 1, wherein the molecular oxygen has a purity degree greater than or equal to 80% volume per volume (v/v) and less than or equal to 97% (v/v).

3. The method of claim 1, wherein the hyaluronic acid has a molecular weight greater than or equal to 200 kilodaltons (kDa) and less than or equal to 2 megadaltons (MDa).

4. The method of claim 1, wherein the molecular oxygen is administered jointly with the hyaluronic acid.

5. The method of claim 4, wherein the molecular oxygen also is administered prior to the joint administration with the hyaluronic acid.

6. The method of claim 1, wherein the molecular oxygen is administered using a flow rate greater than or equal to 0.1 liters per minute (L/min) and less than or equal to 5 L/min.

7. The method of claim 1, wherein the hyaluronic acid is in a form of a salt of a biologically acceptable alkaline metal.

8. The method of claim 7, wherein the hyaluronic acid is in the form of sodium hyaluronate.

9. The method of claim 8, wherein the sodium hyaluronate is administered at a dosage greater than or equal to 10 milligrams (mg) and less than or equal to 100 mg out of a unit of volume of the molecular oxygen, and
wherein a maximum unit of volume of the molecular oxygen is greater than or equal to 1.5 liters (L) and less than or equal to 75 L.

10. The method of claim 8, wherein the sodium hyaluronate is administered together with the molecular oxygen for a time greater than or equal to 5 minutes and less than or equal to 15 minutes.

11. The method of claim 1, wherein the selected vaginal disorder is vaginal dryness.

12. The method of claim 1, wherein the selected vaginal disorder is vulvovaginal atrophy.

* * * * *